US012636104B2

(12) United States Patent
Ballantyne et al.

(10) Patent No.: US 12,636,104 B2
(45) Date of Patent: May 26, 2026

(54) SETUP ARM PITCH JOINT ESTIMATOR

(71) Applicant: Covidien LP, Mansfield, MA (US)

(72) Inventors: Todd A. Ballantyne, Nashua, NH (US); Stefan Joerg, Munich (DE); Paul M. Loschak, Somerville, MA (US)

(73) Assignee: Covidien LP, Mansfield, MA (US)

( * ) Notice: Subject to any disclaimer, the term of this patent is extended or adjusted under 35 U.S.C. 154(b) by 818 days.

(21) Appl. No.: 17/429,491

(22) PCT Filed: Feb. 17, 2020

(86) PCT No.: PCT/US2020/018508
§ 371 (c)(1),
(2) Date: Aug. 9, 2021

(87) PCT Pub. No.: WO2020/172097
PCT Pub. Date: Aug. 27, 2020

(65) Prior Publication Data
US 2022/0151719 A1 May 19, 2022

Related U.S. Application Data

(60) Provisional application No. 62/807,072, filed on Feb. 18, 2019.

(51) Int. Cl.
*A61B 34/37* (2016.01)
*A61B 34/20* (2016.01)
*A61B 90/00* (2016.01)

(52) U.S. Cl.
CPC ...... *A61B 34/37* (2016.02); *A61B 2034/2048* (2016.02); *A61B 2034/2059* (2016.02);
(Continued)

(58) Field of Classification Search
CPC ............ A61B 34/37; A61B 2034/2048; A61B 2034/2059; A61B 2090/371; A61B 2090/376; A61B 2090/378
See application file for complete search history.

(56) References Cited

U.S. PATENT DOCUMENTS

| | | | | |
|---|---|---|---|---|
| 8,828,023 | B2 | 9/2014 | Neff et al. | |
| 2003/0004610 | A1* | 1/2003 | Niemeyer | A61B 34/70 |
| | | | | 700/245 |

(Continued)

FOREIGN PATENT DOCUMENTS

| | | |
|---|---|---|
| CN | 101106952 A | 1/2008 |
| CN | 101421080 A | 4/2009 |

(Continued)

OTHER PUBLICATIONS

International Search Report mailed Jun. 12, 2020 and Written Opinion completed Jun. 12, 2020 corresponding to counterpart Int'l Patent Application PCT/US2020/018508.

(Continued)

*Primary Examiner* — Sihar A Karwan
(74) *Attorney, Agent, or Firm* — Carter, DeLuca & Farrell, LLP

(57) ABSTRACT

A process for determining a pitch angle of a support arm for a linkage of a robot includes receiving accelerometer readings from an inertial measurement unit of an instrument drive unit (IDU) within a frame of the IDU and calculating the pitch angle of the support arm from a horizontal of a base of the robot.

20 Claims, 4 Drawing Sheets

(52) U.S. Cl.

CPC ... *A61B 2090/371* (2016.02); *A61B 2090/376* (2016.02); *A61B 2090/378* (2016.02)

(56) References Cited

U.S. PATENT DOCUMENTS

| | | | |
|---|---|---|---|
| 2007/0089557 | A1 | 4/2007 | Solomon et al. |
| 2010/0204713 | A1 | 8/2010 | Ruiz Morales |
| 2013/0239392 | A1 | 9/2013 | Solomon et al. |
| 2014/0039517 | A1* | 2/2014 | Bowling ................ A61B 34/76 606/130 |
| 2015/0119638 | A1 | 4/2015 | Yu et al. |
| 2019/0167366 | A1* | 6/2019 | Ummalaneni ............ G06T 7/73 |
| 2021/0212777 | A1 | 7/2021 | Cheng |

FOREIGN PATENT DOCUMENTS

| | | | |
|---|---|---|---|
| CN | 104758066 | A | 7/2015 |
| CN | 105078576 | A | 11/2015 |
| CN | 105939647 | A | 9/2016 |
| CN | 109310472 | A | 2/2019 |
| EP | 1815949 | A1 | 8/2007 |
| EP | 2263590 | A2 | 12/2010 |
| EP | 2942029 | A1 | 11/2015 |
| KR | 10-2012-0069333 | A | 6/2012 |
| WO | 0060521 | A1 | 10/2000 |
| WO | 2017210516 | A1 | 12/2017 |
| WO | 2020163263 | A1 | 8/2020 |

OTHER PUBLICATIONS

Chinese Office Action issued in corresponding Chinese Application No. 202080013824.6 dated Apr. 20, 2023, 15 pages.

Extended European Search Report dated Nov. 2, 2022 corresponding to counterpart Patent Application EP 20760083.4.

Communication Pursuant to Article 94(3) EPC issued in corresponding European Application No. 20 760 083.4 dated Feb. 21, 2025, 5 pages.

* cited by examiner

T

J₅

IDU

12D

120

118

116  12C

J₄

126

12

J₃

J₁

3

114

J₂

12A

112

A ─────────────── A

20

T $Z_W$ $F_W$ $X_W$ $Y_W$

10

15

19

$Z_b$

34

18

X $X_b$ $F_b$ $Y_b$

12a

J₁

H

α

A

A

H

112

15

400

DEFINING A HOME CONFIGURATION ⟋210

RECEIVING ACCELEROMETER READINGS ⟋220

ROTATING THE ACCELEROMETER READINGS TO BASE FRAME ⟋230

CALCULATING PITCH ANGLE FROM ACCELEROMETER READINGS ⟋240

SAVE THE PITCH ANGLE ⟋250

USING PITCH ANGLE TO CONTROL A TOOL ⟋260

SETUP ARM PITCH JOINT ESTIMATOR

CROSS-REFERENCE TO RELATED APPLICATIONS

The present application is a U.S. National Stage Application filed under 35 U.S.C. § 371(a) claiming the benefit of and priority to International Patent Application No. PCT/US2020/018508, filed Feb. 17, 2020, which claims the benefit of and priority to U.S. Provisional Patent Application Ser. No. 62/807,072, filed Feb. 18, 2019, the entire disclosures of each of which being incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector of a surgical instrument that acts on a patient. The user interface includes an input controller or handle that is moveable by the surgeon to control the robotic surgical system and a display allowing the surgeon to visualize the surgical instrument within a surgical site.

The surgical instrument is supported by an arm of a surgical robot. The arm of the surgical robot includes a setup arm and a linkage that are movable within the surgical environment to manipulate the surgical instrument. The linkage is supported by the setup arm and supports the surgical instrument within the surgical environment. The setup arm may move during the surgical procedure to reposition the linkage and/or to avoid collisions with other arms of the surgical robot.

There is a need for determining the position and/or pose of the setup arm within the surgical environment to determine the position of the surgical instrument and thus, control the surgical instrument during a surgical procedure. Thus, there is a continuing need for determining the pose of the setup arm within the surgical environment during a surgical procedure.

SUMMARY

This disclosure relates generally to systems and methods for determining the pose, in particular the pitch, of a setup arm of a surgical robot within the surgical environment using one or more sensors of a linkage supported by the setup arm.

In an aspect of the present disclosure, a process for determining a pitch angle of a support arm for a linkage of a robot includes receiving accelerometer readings from an inertial measurement unit of an instrument drive unit (IDU) within a frame of the IDU, rotating the accelerometer readings from the frame of the IDU to a frame of the support arm which supports the linkage which supports the IDU, and calculating the pitch angle of the support arm from a horizontal of a base of the robot.

In aspects, the process includes defining a home configuration of the linkage of the robot. Rotating the accelerometer readings may include rotating the accelerometer readings about a joint of the linkage from a home configuration of the joint.

In some aspects, rotating the accelerometer readings to the frame of the support arm includes rotating the accelerometer readings by rotation of a first link of the linkage about a first joint between the first link and the support arm. Rotating the accelerometer readings to the frame of the support arm may include rotating the accelerometer readings by rotation of a second link of the linkage about a second joint between the second link and the first link. Rotating the accelerometer readings to the frame of the support arm may include rotating the accelerometer readings by rotation of the IDU about a tool axis that passes through the IDU.

In particular aspects, receiving the accelerometer readings includes the accelerometer readings being indicative of gravity acting on the IDU. The process may include repeating receiving accelerometer readings, rotating the accelerometer readings to the frame of the support arm, and calculating the pitch angle of the support arm and applying a low pass filter to the calculated pitch angels. Applying the low pass filter to the calculated pitch angles may include the low pass filter having a cutoff of about 1 Hz.

In another aspect of the present disclosure, a process for controlling a surgical robot includes receiving a control signal indicative of a desired movement of a tool of the surgical robot, receiving accelerometer readings from an IDU of the surgical robot, determining a pitch angle of the surgical robot from a horizontal based on the accelerometer readings, and transmitting a control signal incorporating the pitch angle to the IDU to activate a motor of the IDU.

In aspects, determining the pitch angle of the surgical robot includes rotating the accelerometer readings form the frame of the IDU to a frame of a support arm which supports a linkage of the surgical robot, the linkage supporting the IDU. The process may include determining a status of a brake of the surgical robot is engaged before determining the pitch angle of the surgical robot.

In some aspects, the process includes determining a status of a brake of the surgical robot is released and entering a manual mode of gravity compensation which includes continually calculating the pitch angle. The process may include applying a low pass filter to the continually calculated pitch angles.

In particular aspects, the process includes allowing the pitch angle of the surgical robot to settle for a threshold time before transmitting the control signal.

In another aspect of the present disclosure, a robotic surgical system includes a base, a support arm extending from the base, a linkage supported by the support arm, an instrument drive unit (IDU) supported by the linkage, and a processing unit. The IDU includes an inertial measurement unit that is configured to generate accelerometer readings and a motor. The processing unit is configured to receive the accelerometer readings and to determine a pitch angle of the support arm from a horizontal based on the accelerometer readings. The processing unit is further configured to transmit a control signal, which incorporates the pitch angle, to the IDU to activate the motor of the IDU.

In aspects, the base includes a brake that has an engaged configuration in which the support arm is prevented from moving and a released configuration in which the support arm is movable.

In some aspects, the linkage includes a first link, a second link, a third link, and a rail. The first link may have a first portion that is supported by the support arm about a first joint and a second portion. The second link may have a first portion that that is supported by the second portion of the first link about a second joint and a second portion. The third link may have a first portion that is supported by the second portion of the second link about a third joint and a second portion. The rail may be supported by the second portion of the third link. The IDU may be slidably supported by the rail.

In certain aspects, the processing unit may include a controller that is disposed within the base.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
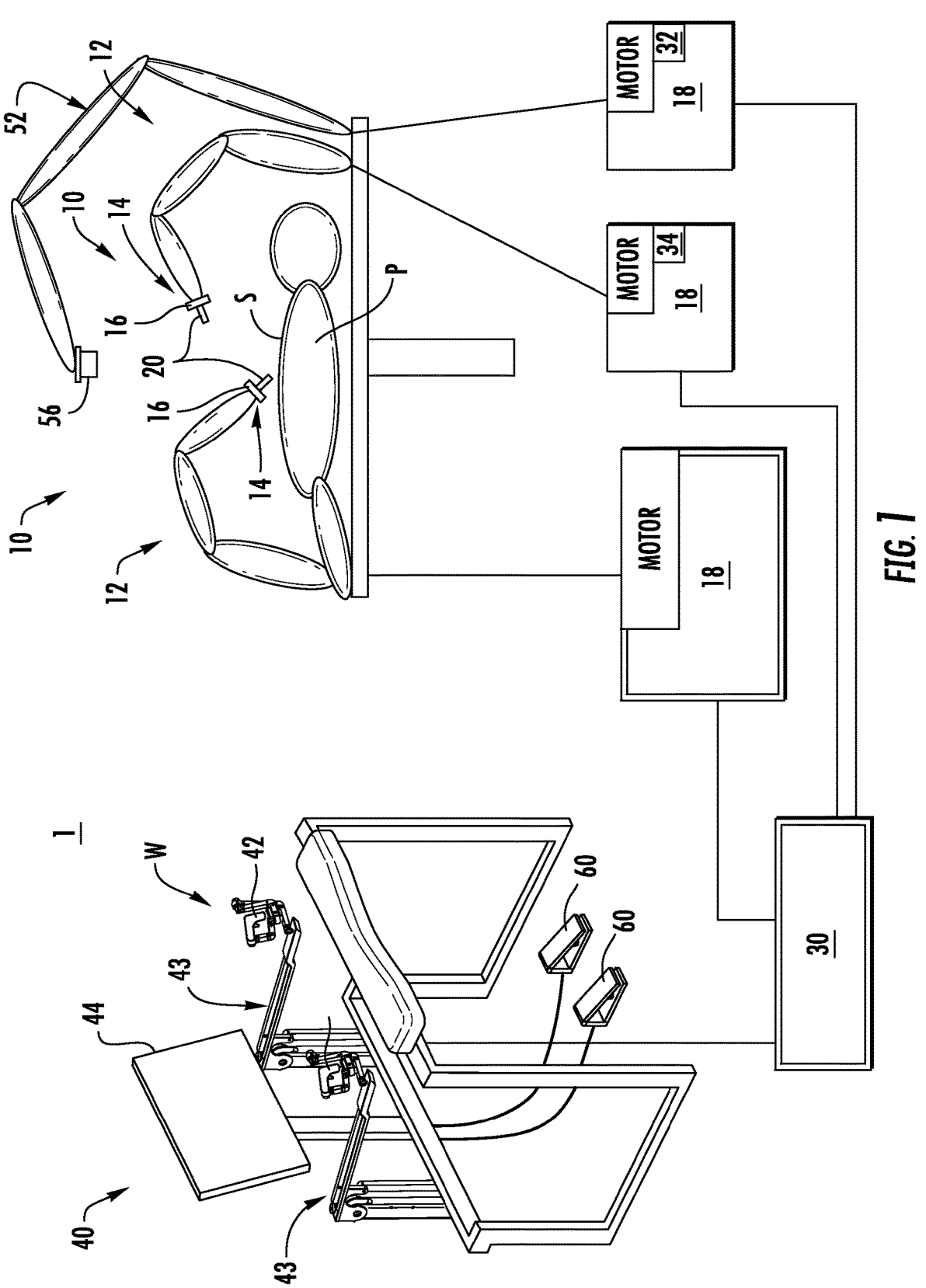
FIG. 1 is a schematic of an exemplary robotic surgical system provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel.

Referring to FIG. 1, a robotic surgical system 1 in accordance with the present disclosure is shown generally as a surgical robot 10, a processing unit 30, and a user console 40. The surgical robot 10 generally includes linkages or arms 12 and one or more robot bases 18 that each support one of the linkages 12. The linkages 12 moveably support an end effector or tool 20 which is configured to act on tissue. The linkages 12 each have an end 14 that supports the end effector or tool 20 which is configured to act on tissue. In addition, the ends 14 of the linkages 12 may include an imaging device 16 for imaging a surgical site "S". The user console 40 is in communication with the robot bases 18 through the processing unit 30. In addition, the robot bases may each include a controller 32, 34 that is in communication with the processing unit 30.

The user console 40 includes a display device 44 which is configured to display three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user console 40 also includes input handles 42 which are supported on control arms 43 which allow a clinician to manipulate the surgical robot 10 (e.g., move the linkages 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices (not explicitly shown) which allow the surgeon to manipulate (e.g., clamp, grasp, fire, open, close, rotate, thrust, slice, etc.) the tools 20 supported at the ends 14 of the linkages 12.

Each of the input handles 42 is moveable through a predefined workspace to move the ends 14 of the linkages 12, e.g., tools 20, within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to the view captured by the imaging devices 16, 56. In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

Figures 2, 3:
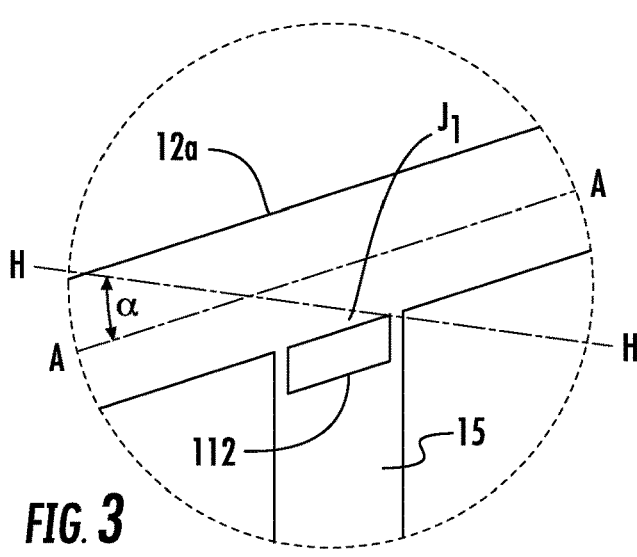
FIG. 2 is a side view of a robot base or cart of a surgical robot of the robotic surgical system of FIG. 1.
FIG. 3 is an enlarged view of the indicated area of detail of FIG. 2.

Referring to FIG. 2, the surgical robot 10, shown as a robot base or cart 18, has a world frame $F_w$ that is a fixed frame defined by $X_w$-$Y_w$-$Z_w$ axes which remains fixed during a surgical procedure. The world frame $F_w$ is a frame positioned on the floor or ground of a surgical environment that can be reference by other frames within the surgical environment allowing each frame within the surgical environment a common frame of reference. As shown, the $X_w$ axis is defined in a horizontal direction parallel to the floor, the $Y_w$ axis is defined in a horizontal direction parallel to the floor, and the $Z_m$ axis is defined in a height direction from the floor to the ceiling. It will be appreciated that the $X_w$ and the $Y_w$ axes define an X-Y plane that is parallel to the floor. In addition, the robot base 18 defines a base frame $F_b$ that is defined by $X_b$-$Y_b$-$Z_b$ axes which are defined by the base 18. As shown, the $X_b$ axis is defined in a horizontal direction parallel to the floor and parallel to the $X_w$ axis, the $Y_b$ axis is defined in a horizontal direction parallel to the floor and parallel to the $Y_w$ axis, and the $Z_b$ axis is defined in a height direction from the floor to the ceiling and parallel to the $Z_w$ axis. It will be appreciated that the $X_b$ and the $Y_b$ axes are within the X-Y plane with the intersection of the $X_b$ and $Y_b$ axes offset from the intersection of the $X_w$ and $Y_w$ axes.

The robot base 18 includes a setup arm 15 that supports a first portion of a first link 12a of the linkage 12 at a first joint $J_1$ such that a longitudinal axis A-A of the first link 12a is substantially parallel to the X-Y plane defined. The first joint $J_1$ is a single degree of freedom joint which allows the first link 12$a$ to rotate about the first joint about an axis that is substantially orthogonal to the X-Y plane. With additional reference to FIG. 3, it will be appreciated that the first link 12$a$ may be pitched slightly at the first joint $J_1$ such that the longitudinal axis A-A is out of parallel with a horizontal axis H-H that is parallel to the X-Y plane to define a pitch angle $\alpha$. The pitch angle $\alpha$ indicates the amount that the first link 12$a$, and thus the setup arm 15, is pitched relative to the horizontal axis H-H. The pitch angle $\alpha$ may be the result of manufacturing tolerances of the robot base 18, the weight of the linkage 12 and/or tool 20 cantilevered from the setup arm 15, and/or the robot base 18 being supported on the floor or ground in a non-level manner. The robot base 18 also includes a brake 19 that has an engaged configuration in which the brake 19 prevents movement of the setup arm 15 and a disengaged or released configuration in which movement of the setup arm 15 is permitted. In some embodiments, the first link 12$a$ may be directly secured to the robot base 18 such that the pitch angle $\alpha$ is defined between a longitudinal axis of the first link 12$a$ and the horizontal H-H.

As detailed below, the linkage 12 includes a plurality of sensors that can be used to determine the pitch angle $\alpha$. The pitch angle $\alpha$ may be used as an input for control algorithms that to control position and movement of the tool 20. For example, forward or inverse kinematics may be used to control the position of the tool 20 within the world frame $F_w$. In addition, the hand-eye coordination calculations may be used to control the position of the tool 20 within the world frame $F_w$. For a detailed discussion of exemplary kinematic control algorithms, reference can be made to U.S. patent application Ser. No. 16/081,773, filed Aug. 31, 2018, and for a detailed discussion of exemplary hand-eye coordination calculation reference can be made to U.S. Provisional Patent Application Ser. No. 62/801,734, filed Feb. 6, 2019. The entire contents of each of the above applications are hereby incorporated by reference.

With continued reference to FIG. 2, the linkage 12 includes the first link 12$a$, a second link 12$b$, a third link 12$c$, and a fourth link or rail 12$d$. Each link is pivotally coupled to at least one other link about a single degree of freedom joint as detailed below. The second link 12$b$ includes a first portion that is pivotally coupled to a second portion of the first link 12$a$ by a second joint $J_2$ and a first portion of the third link 12$c$ is pivotally coupled to a second portion of the second link by a third joint $J_3$. The second and third links 12$b$, 12$c$ are pivotal about axes of the second and third joints $J_2$, $J_3$ that are parallel to one another and perpendicular to the axis of the first joint $J_1$. In embodiments, movement of the second and third links 12$b$, 12$c$ about the second and third joints $J_2$, $J_3$ is linked such that movement of the second link 12$b$ about the second joint $J_2$ is equal and opposite to movement of the third link 12$c$ about the third joint $J_3$ such that the third link 12$c$ remains parallel to the first link 12$b$. The fourth link 12$d$ is coupled to a second portion of the third link 12$c$ about a fourth joint $J_4$. Movement of the fourth link 12$d$ about the fourth joint $J_4$ is about an axis parallel to the axes of the second and third joints $J_2$, $J_3$.

The linkage 12 includes an instrument drive unit (IDU) that is slidably supported along the fourth link 12$d$ to define a linear fifth joint $J_5$ which allows the IDU to move along a tool axis T-T that is parallel to a longitudinal axis of the fourth link 12$d$. A sixth joint $J_6$ is a roll joint of the IDU about the tool axis T-T which permits the IDU, and thus the tool 20, to rotate about the tool axis T-T.

One or more of the joints $J_1$-$J_6$ may include sensors to determine the position or joint angles of the respective joint. For example, the first joint $J_1$ includes a first sensor 112 that is configured to determine the position of the first link 12$a$ relative to the setup arm 15 about the first joint $J_1$. The second joint $J_2$ includes a second sensor 114 that is configured to determine the position of the second link 12$b$ relative to the first link 12$a$ about the second joint $J_2$. The fifth joint $J_5$ includes a third sensor 116 that is configured to determine the position of the IDU along the rail 12$d$. The sixth joint $J_6$ includes a fourth sensor 118 that is configured to determine a roll of the IDU about the tool axis T-T. In embodiments, the first, second, third, and fourth sensors 112, 114, 116, 118 may be encoders or potentiometers which determine the joint angle of the respective joint $J_1$, $J_2$, $J_5$, $J_6$. In addition, the IDU includes an inertial measurement unit (IMU) 120 that may be an accelerometer that is configured to determine the inertia of the IDU, e.g., to determine the gravitational forces on the IDU.

Figure 4:
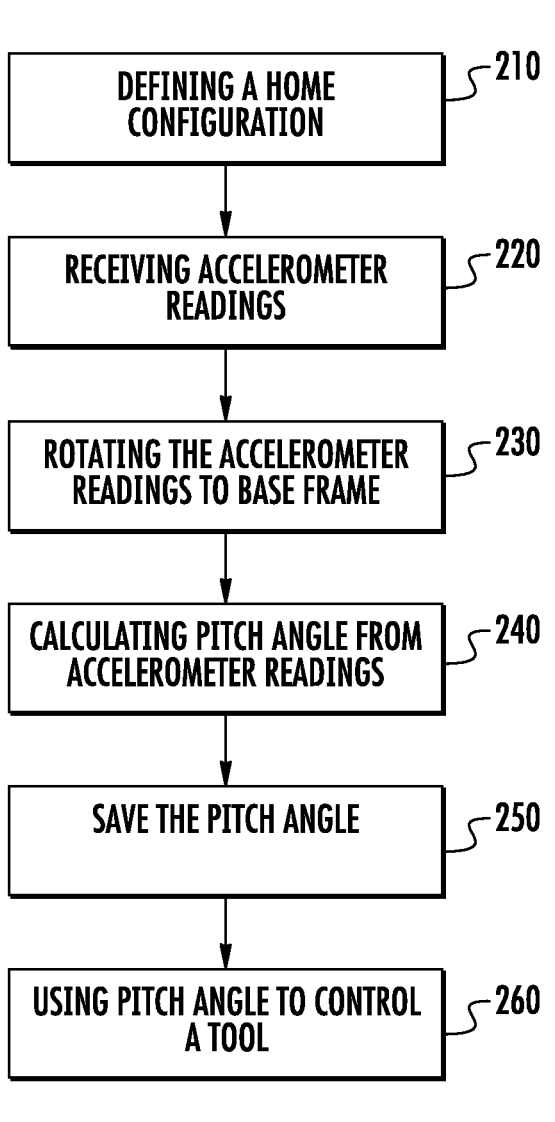
FIG. 4 is a flow chart of a process for calculating a pitch angle of the surgical robot of FIG. 3 in accordance with the present disclosure.

Referring now to FIG. 4, a process or method 200 of determining the pitch angle $\alpha$ of the setup arm 15 at the first joint $J_1$ is provided in accordance with the present disclosure with reference to the robotic surgical system of FIGS. 1-3. The method 200 may be controlled by the processing unit 30 or within the controller 34 of the base or cart 18. As detailed below, the method 200 uses the inertia measured by the IMU 120 and the joint angles of the joints of the linkage 12, e.g., joints $J_1$, $J_2$, $J_5$, $J_6$, to determine the pitch angle $\alpha$. Initially, a home configuration of the linkage 12, as shown in FIG. 2, is defined (Step 210). In the home configuration, the first link 12$a$ extends from the setup arm 15 in a direction away from the base 18, the first and third links 12$a$, 12$c$ are parallel to one another and spaced apart in a vertical direction from one another, and the rail 12$d$ is positioned perpendicular to the third link 12$c$ about the fourth joint $J_4$. The joint angles of the joints $J_1$, $J_2$, $J_5$, $J_6$ in the home configuration are considered to be the zero values for each of the respective joints $J_1$, $J_2$, $J_5$, $J_6$.

With the home configuration of the linkage 12 defined, the accelerometer readings $ACC_{IMU}$ from the IMU 120 in a frame of the IDU are received in the processing unit 30 or the controller 34 (Step 220). The accelerometer readings $ACC_{IMU}$ are received in the x, y, z coordinates in a frame of the IDU as follows:

$$ACC_{IMU} = \begin{bmatrix} 0 & 0 & -1 \\ 0 & 1 & 0 \\ -1 & 0 & 0 \end{bmatrix} \begin{bmatrix} x \\ y \\ z \end{bmatrix}$$

where x, y, z are the readings from the IMU 120 taken in a frame of the IDU.

The accelerometer readings $ACC_{IMU}$ are then transformed from the frame of the IDU to the base frame $F_b$ using the joint angles of the first, second, and sixth joints $J_1$, $J_2$, $J_6$ (Step 230). To transform the accelerometer readings $ACC_{IMU}$ to the base frame $F_b$ the rotation of each joint $J_1$, $J_2$, $J_6$ is applied to the accelerometer readings $ACC_{IMU}$ to provide an acceleration vector in the base frame $ACC_b$ as:

$$ACC_b = R_{j1}R_{j2}R_{j6}ACC_{IMU}$$

The rotation about each joint is represented as follows:

$$R_{J1} = \begin{bmatrix} 1 & 0 & 0 \\ 0 & c_{J1} & -s_{J1} \\ 0 & s_{J1} & c_{J1} \end{bmatrix} \quad R_{J2} = \begin{bmatrix} c_{J2} & 0 & s_{J2} \\ 0 & 1 & 0 \\ -s_{J2} & 0 & c_{J2} \end{bmatrix} \quad R_{J6} = \begin{bmatrix} c_{J6} & -s_{J6} & 0 \\ s_{J6} & c_{J6} & 0 \\ 0 & 0 & 1 \end{bmatrix}$$

where "c" and "s" are cosine and sine, respectively. The acceleration vector $ACC_b$ is then used to calculate the pitch angle $\alpha$ relative to the horizontal H-H which is parallel to the X-Y plane (Step 240) as follows:

$$\alpha = a\tan2(\|ACC_N \times g_N\|, \; ACC_N \cdot g_N) \text{ where}$$

$$ACC_N = \frac{ACC_b}{\|ACC_b\|}, \; g = \begin{bmatrix} 0 \\ 0 \\ -9.81 \end{bmatrix}, \text{ and } g_N = \frac{g}{\|g\|}.$$

and where $\widehat{SA}_{pitch} = \text{sign}(ACC_{N,x})^* \, \widehat{SA}_{Pitch}$, and where $ACC_{N,x}$ refers to the x-component of the $ACC_N$ vector, and the "sign" function is taking the + or − sign of that value. In other words, the SA pitch angle is multiplied by either +1 or −1 depending on the "sign" of the x-component of the acceleration vector.

When the pitch angle $\alpha$ is determined, the pitch angle $\alpha$ may be verified by repeating the calculations with updated accelerometer readings from the IMU 120 (Step 250). This may be repeated until the calculation of the pitch angle $\alpha$ settles out, e.g., remains the same for a threshold period of time or number of calculations. The threshold period of time may be about three seconds. Additionally or alternatively, a low pass filter with a cutoff of about 1 Hz may be applied to calculations of the pitch angle $\alpha$ until the pitch angle $\alpha$ settles out.

The pitch angle $\alpha$ is then saved for the position of the setup arm 15 of the robot base 18 (Step 250). The pitch angle $\alpha$ can be used in control algorithms to control the tool 20, e.g., movement or a function of the tool 20 during a surgical procedure as detailed below (Step 260).

Figure 5:
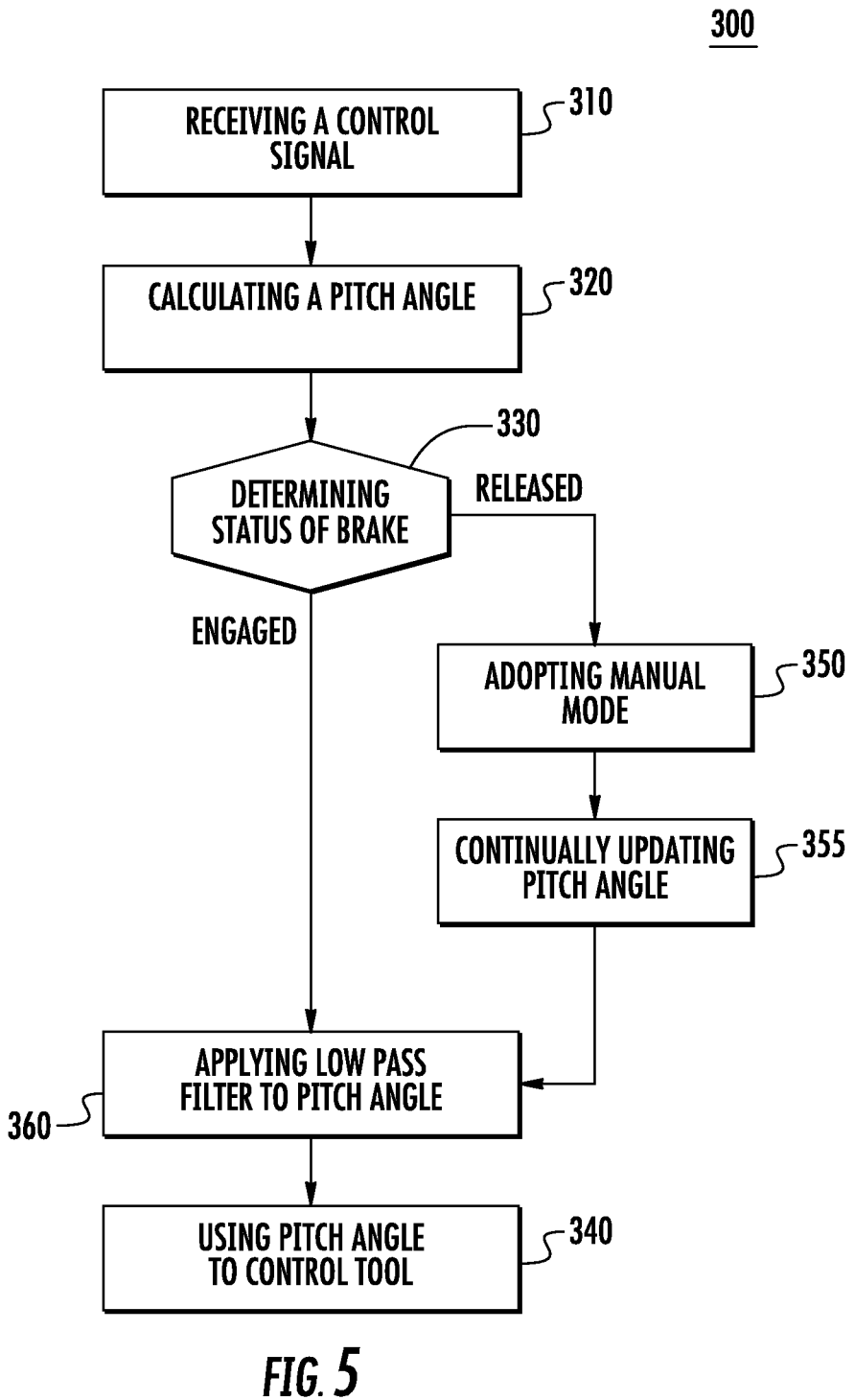
FIG. 5 is a flow chart of a process for controlling the robotic surgical system of FIG. 1 in accordance with the present disclosure.

Referring to FIG. 5, a process or method 300 of controlling the surgical robot 10 is provided in accordance with the present disclosure with reference to the robotic surgical system 1 of FIGS. 1-3 with the processing unit 30 and/or the controller 34. Initially, a control signal is received from the user console 40 (Step 310). When the control signal is received the pitch angle $\alpha$ is determined using the method 200 as detailed above (Step 320). The processing unit 30 then determines the status of the brake 19 of the setup arm 15 (Step 330). When the brake 19 is engaged, or TRUE, the pitch angle $\alpha$ is valid such that the pitch angle $\alpha$ can be used for control algorithms to move the tool 20 in response to the control signals (Step 340).

When the brake 19 is released, or FALSE, the pitch angle $\alpha$ may fluctuate as the setup arm 15 moves. For example, the brake 19 may be released to allow the setup arm 15 and/or the linkage 12 to move to reposition the setup arm 15 and/or the linkage 12 and/or to avoid a collision with another object within the surgical environment, e.g., another setup arm 15 or linkage 12. When the brake 19 is released the processing unit 30 may adopt a manual mode of gravity compensation such that the pitch angle $\alpha$ is continually calculated to compensate for potential changes in the pitch angle $\alpha$ (Step 350). The method 200 may be used to continually calculate the pitch angle $\alpha$. In addition, the processing unit 30 may apply a low pass filter to the pitch angle $\alpha$ to avoid unintended movements of the tool 20 and/or until the calculated pitch angle $\alpha$ settles out (Step 355). The low pass filter may be a first order filter with a cutoff frequency in the range of about 1 Hz (Step 360). When the pitch angle $\alpha$ settles out or passes through the low pass filter, the pitch angle $\alpha$ may be used for the control algorithms to move the tool 20 in response to the control signals (Step 340).

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A process for determining a pitch angle of a support arm for a linkage of a robot, the process comprising:
defining a home configuration of the linkage, wherein the linkage includes a first link, a second link and a third link, wherein the first link and the third link of the linkage are parallel to one another and spaced apart from one another, and wherein a rail of the linkage is positioned perpendicular to the third link about a linear joint coupling a portion of the third link to the rail;
receiving accelerometer readings from an inertial measurement unit (IMU) of an instrument drive unit (IDU) including coordinates within an inertial frame of the IDU, wherein the IDU is slidably supported on the rail of the linkage, and wherein the IMU is integrated within the IDU;
transforming the accelerometer readings from the inertial frame of the IDU to a rotating frame of the support arm which supports the linkage, wherein transforming the accelerometer readings includes rotating the coordinates of the accelerometer readings about the linear joint of the linkage from the home configuration of the linkage;
determining a normalized acceleration vector from the transformed accelerometer readings; and
calculating the pitch angle of the support arm from a horizontal plane of a base of the robot by comparing the normalized acceleration vector with a gravity reference vector.

2. The process according to claim 1, wherein transforming the accelerometer readings to the rotating frame of the support arm further includes rotating the coordinates of the accelerometer readings by applying a first rotation matrix corresponding to a rotation of the first link of the linkage about a first joint between the first link and the support arm.

3. The process according to claim 2, wherein transforming the accelerometer readings to the rotating frame of the support arm further includes rotating the coordinates of the accelerometer readings by applying a second rotation matrix corresponding to a rotation of the second link of the linkage about a second joint between the second link and the first link.

4. The process according to claim 2, wherein transforming the accelerometer readings to the rotating frame of the support arm further includes rotating the coordinates of the accelerometer readings by applying a third rotation matrix corresponding to a rotation of the IDU about a tool axis that passes through the IDU.

5. The process according to claim 1, wherein receiving the accelerometer readings includes the accelerometer readings being indicative of gravity acting on the IDU, and wherein the IDU is structurally distinct and separate from a sensor disposed on a joint of the linkage.

6. A process for controlling a surgical robot, the process comprising:

receiving a control signal indicative of a desired movement of a tool of the surgical robot;

receiving accelerometer readings from an inertial measurement unit (IMU) of an instrument drive unit (IDU) of the surgical robot including coordinates within an inertial frame of the IDU, wherein the IDU is slidably supported on a rail of the surgical robot, and wherein the IMU is physically integrated within the IDU;

receiving position data from a sensor disposed on a joint of a linkage of the surgical robot which supports the rail, the position data including an angle of the joint of the linkage, wherein the angle indicates a rotation of the linkage about the joint;

determining a normalized acceleration vector from transformed accelerometer readings;

determining a pitch angle of the surgical robot from a horizontal plane based on the accelerometer readings and the position data by comparing the normalized acceleration vector with a gravity reference vector; and transmitting a control signal incorporating the pitch angle to the IDU to activate a motor of the IDU.

7. The process according to claim 6, wherein determining the pitch angle of the surgical robot includes transforming the accelerometer readings from the inertial frame of the IDU to a rotating frame of a support arm which supports the linkage of the surgical robot, the linkage supporting the IDU, and wherein the IDU is structurally distinct and separate from the sensor disposed on a joint of the linkage.

8. The process according to claim 6, further comprising determining a status of a brake of the surgical robot is engaged before determining the pitch angle of the surgical robot.

9. The process according to claim 6, further comprising:
determining a status of a brake of the surgical robot is released; and
entering a manual mode of gravity compensation including continually calculating the pitch angle.

10. The process according to claim 9, further comprising applying a low pass filter to the continually calculated pitch angles.

11. The process according to claim 6, further comprising allowing the pitch angle of the surgical robot to settle for a threshold time before transmitting the control signal.

12. The process according to claim 6, further comprising applying a low pass filter to the pitch angle before transmitting the control signal.

13. A robotic surgical system comprising:
a base;
a support arm extending from the base;
a linkage supported by the support arm;
a sensor disposed on a joint of the linkage, the sensor configured to generate position data;
an instrument drive unit (IDU) supported by the linkage, the IDU including an inertial measurement unit (IMU) configured to generate accelerometer readings and a motor, wherein the IMU is integrated within the IDU; and
a processing unit configured to:
receive the accelerometer readings including coordinates within an inertial frame of the IDU;
receive the position data from the sensor disposed on the joint of the linkage, the position data including an angle of the joint, wherein the angle indicates a rotation of the linkage about the joint;

transform the accelerometer readings from the inertial frame of the IDU based on the position data to a rotating frame of the support arm to determine an acceleration vector;

determine a normalized acceleration vector from the transformed accelerometer readings; and calculate a pitch angle of the support arm from a horizontal axis based on the acceleration vector by comparing the normalized acceleration vector with a gravity reference vector, the processing unit further configured to transmit a control signal, which incorporates the pitch angle, to the IDU to activate the motor of the IDU.

14. The robotic surgical system according to claim 13, wherein the base includes a brake having an engaged configuration in which the support arm is prevented from moving and a released configuration in which the support arm is movable.

15. The robotic surgical system according to claim 13, wherein the linkage includes a first link, a second link, a third link, and a rail, the first link having a first portion supported by the support arm about a first joint and a second portion, the second link having a first portion supported by the second portion of the first link about a second joint and a second portion, the third link having a first portion supported by the second portion of the second link about a third joint and a second portion, the rail supported by the second portion of the third link about a linear joint, the IDU slidably supported by the rail about a roll joint, wherein the IDU is rotatable about a sixth joint defined along a tool axis defined by a length of the IDU, the rail positioned parallel to the tool axis.

16. The process according to claim 1, further comprising:
receiving position data from a plurality of sensors disposed on a plurality of joints of the linkage, the position data including angles of the plurality of joints,
wherein rotation of the first link, the second link, and the IDU are based on the position data; and
determining an acceleration vector in the rotation frame based on the transformed accelerometer readings, wherein calculating the pitch angle is based on the acceleration vector.

17. The robotic surgical system according to claim 15, wherein the sensor includes a first sensor, a second sensor, a third sensor, and a fourth sensor, the first sensor coaxially aligned with a longitudinal axis defined by the first link and the fourth sensor coaxially aligned with the tool axis.

18. The robotic surgical system according to claim 17, wherein the first sensor is disposed on the first joint and configured to determine a rotation of the first link relative to the support arm, the second sensor is disposed on the second joint and configured to determine a rotation of the second link relative to the first link, the third sensor is disposed on the linear joint and configured to determine a linear displacement of the IDU along the rail, and the fourth sensor is disposed on the roll joint and configured to determine a roll of the IDU about the tool axis.

19. The process according to claim 1, further comprising adjusting the calculated pitch angle by multiplying the calculated pitch angle by a sine value determined from a component of the normalized acceleration vector.

20. The process according to claim 1, further comprising verifying the pitch angle until a calculation of the pitch angle settles for a threshold period of time of at least three seconds, wherein verifying further includes repeating receiving accelerometer readings, transforming the accelerometer readings to the rotating frame of the support arm, calculating the pitch angle of the support arm, and applying a low pass filter to the calculated pitch angles.

\* \* \* \* \*